United States Patent
Baller et al.

(10) Patent No.: US 7,652,586 B2
(45) Date of Patent: Jan. 26, 2010

(54) EARLY FOULING DETECTION

(75) Inventors: Marko Baller, Bavaria (DE); Marcin Alexy, Bavaria (DE); Glenn S. Claydon, Wynantskill, NY (US); Peter Joseph Codella, Niskayuna, NY (US); Stacey Kennerly, Niskayuna, NY (US); Kuna Kishore, Bangalore (IN); Anis Zribi, Rexford, NY (US); Guiju Song, Shanghai (CN); Shivappa Goravar, Karnataka (IN); Ajit Achuthan, Schenectady, NY (US)

(73) Assignee: General Electric Company, Niskayuna, NY (US)

( * ) Notice: Subject to any disclaimer, the term of this patent is extended or adjusted under 35 U.S.C. 154(b) by 522 days.

(21) Appl. No.: 11/504,739

(22) Filed: Aug. 15, 2006

(65) Prior Publication Data

US 2008/0041139 A1  Feb. 21, 2008

(51) Int. Cl.
G08B 21/00 (2006.01)
G01R 27/26 (2006.01)
G01F 1/68 (2006.01)
B60H 1/00 (2006.01)
G05D 23/00 (2006.01)

(52) U.S. Cl. ........................ 340/635; 340/602; 340/604; 324/663; 73/204.26; 165/11.1; 236/94

(58) Field of Classification Search .................. None
See application file for complete search history.

(56) References Cited

U.S. PATENT DOCUMENTS

| | | | |
|---|---|---|---|
| 3,665,301 A | 5/1972 | Maltby | |
| 3,913,378 A | 10/1975 | Hausler | |
| 4,147,620 A * | 4/1979 | Artiano et al. | 209/590 |
| 4,485,450 A | 11/1984 | Characklis et al. | |
| 4,766,553 A * | 8/1988 | Kaya et al. | 702/182 |
| 4,912,332 A | 3/1990 | Siebel et al. | |
| 4,942,364 A * | 7/1990 | Nishijima et al. | 324/696 |
| 5,185,533 A | 2/1993 | Banks et al. | |
| 5,619,193 A * | 4/1997 | Doherty et al. | 340/905 |
| 5,985,454 A * | 11/1999 | McMordie et al. | 428/413 |
| 6,023,070 A | 2/2000 | Wetegrove et al. | |
| 6,094,981 A * | 8/2000 | Hochstein | 73/170.17 |
| 6,241,383 B1 | 6/2001 | Feller et al. | |

(Continued)

FOREIGN PATENT DOCUMENTS

EP  0873921 A2 *  4/1998

(Continued)

OTHER PUBLICATIONS

PCT International Search Report dated Jan. 31, 2008.

*Primary Examiner*—Julie Lieu
(74) *Attorney, Agent, or Firm*—Mary Louise Gioeni

(57) ABSTRACT

According to one embodiment, a first capacitive element may be provided and associated with a surface where a fouling layer is to be detected. A second capacitive element may also be provided, and a capacitance between the first and second capacitive elements may be used to detect formation of the fouling layer. According to another embodiment, a thermal device is provided proximate to a surface where a fouling layer is to be detected. A detector (e.g., a thermometer or vibration detector) may detect a condition associated with the surface, and formation of the fouling layer may be determined based at least in part on the condition.

11 Claims, 11 Drawing Sheets

U.S. PATENT DOCUMENTS

| | | |
|---|---|---|
| 6,312,644 B1 | 11/2001 | Moriarty et al. |
| 6,790,664 B2 | 9/2004 | Bailey et al. |
| 7,017,419 B2 * | 3/2006 | Pedersen et al. ............... 73/718 |
| 7,030,982 B1 * | 4/2006 | Woollam et al. ............ 356/369 |
| 7,400,267 B1 * | 7/2008 | Doherty et al. ............. 340/905 |
| 2003/0183536 A1 | 10/2003 | Eden |
| 2006/0061485 A1 * | 3/2006 | Doherty et al. ............. 340/905 |
| 2006/0268273 A1 * | 11/2006 | Woollam et al. ............ 356/369 |
| 2007/0113644 A1 * | 5/2007 | Manaka et al. ........... 73/204.26 |

FOREIGN PATENT DOCUMENTS

| | | |
|---|---|---|
| JP | 60135749 A | 7/1985 |
| JP | 61027445 A | 2/1986 |
| JP | 9236397 A | 9/1997 |
| JP | 2003287396 A | 10/2003 |
| WO | WO 02/28517 A1 | 4/2002 |

* cited by examiner

EARLY FOULING DETECTION

BACKGROUND

Some devices use liquids to perform various functions. Consider, for example, a heat exchanger 100 such as the one illustrated in FIG. 1. The heat exchanger 100 may have a first surface 110 (e.g., at 100° Celsius(C.)) and a second surface 120 (e.g., at 50° C.) and might use water or other liquids stored in, or moving through, internal channels or chambers to facilitate a transfer of heat.

Impurities and contaminants in the liquid may form on surfaces within the heat exchanger 100. This "fouling layer" 102 might include organic, inorganic, and/or biological material. For example, organic deposits might include polymers and inorganic materials might include Calcite.

Eventually, the fouling layer 102 may grow thick enough to substantially decrease performance of the heat exchanger 100 (e.g., the energy efficiency of the device may be substantially reduced). By this point, however, removing the relatively thick fouling layer 102 can be a time consuming and expensive process. For example, a factory might need to be shut down while a massive chemical cleaning of the heat exchanger is performed.

SUMMARY

According to some embodiments, a first capacitive element may be provided for a surface where a fouling layer is to be detected. A second capacitive element may also be provided, and a capacitance between the first and second capacitive elements may be used to detect formation of the fouling layer.

Some embodiments include: means for measuring a capacitance between a first capacitive element associated with a surface and a second capacitive element; and means for determining that a fouling layer has formed on the surface based at least in part on the measured capacitance.

Other embodiments provide a surface where a fouling layer is to be detected, and a thermal device may provide heat proximate to the surface. A detector may detect a condition associated with the surface, and formation of the fouling layer may be determined based at least in part on the condition.

Yet other embodiments comprise: means for providing thermal energy proximate to a surface where a fouling layer is to be detected; means for detecting a condition associated with the surface; means for determining that the fouling layer has formed based at least on part on the condition.

DETAILED DESCRIPTION

Figure 1:
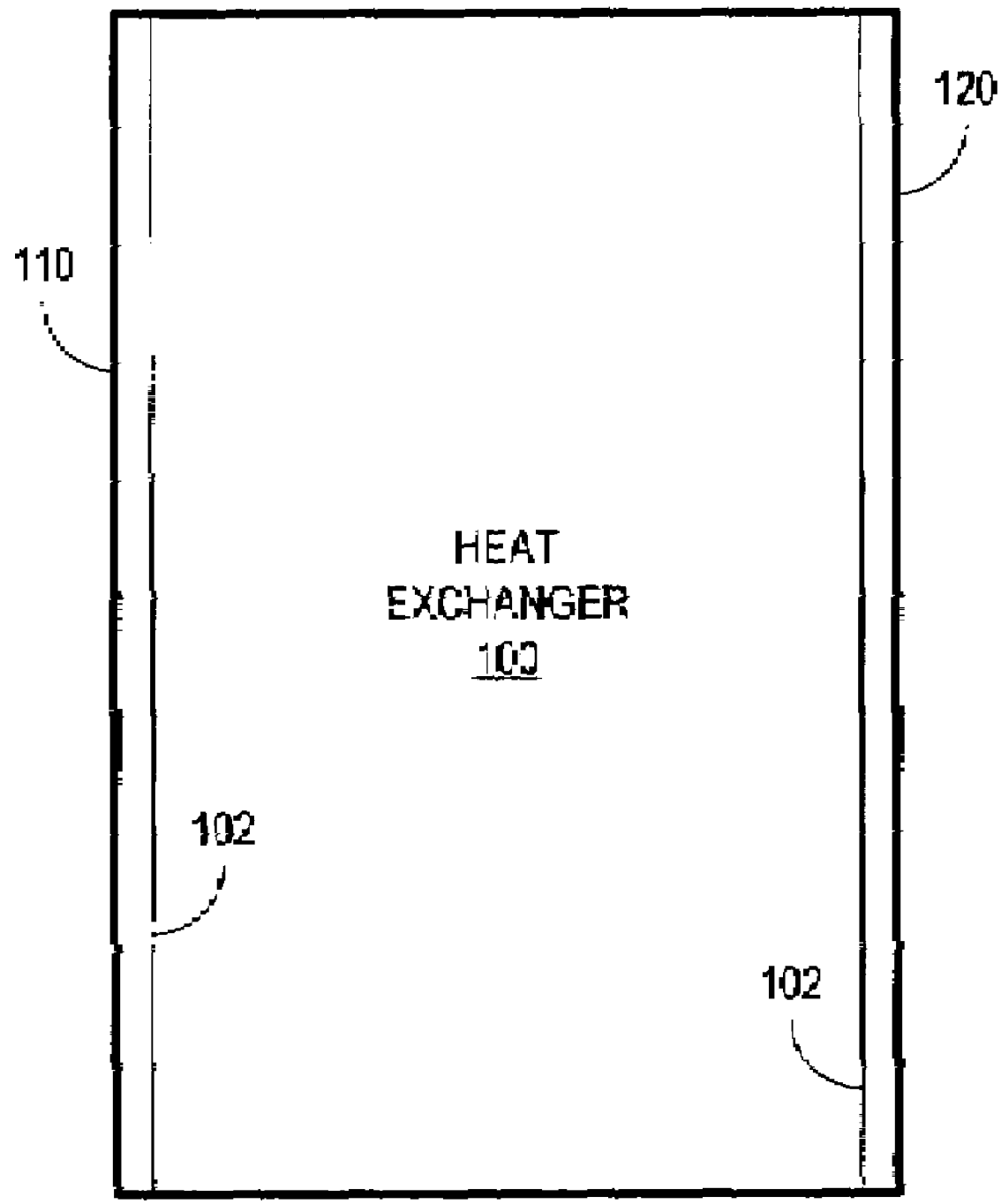
FIG. 1 illustrates a heat exchanger.
Figure 2:
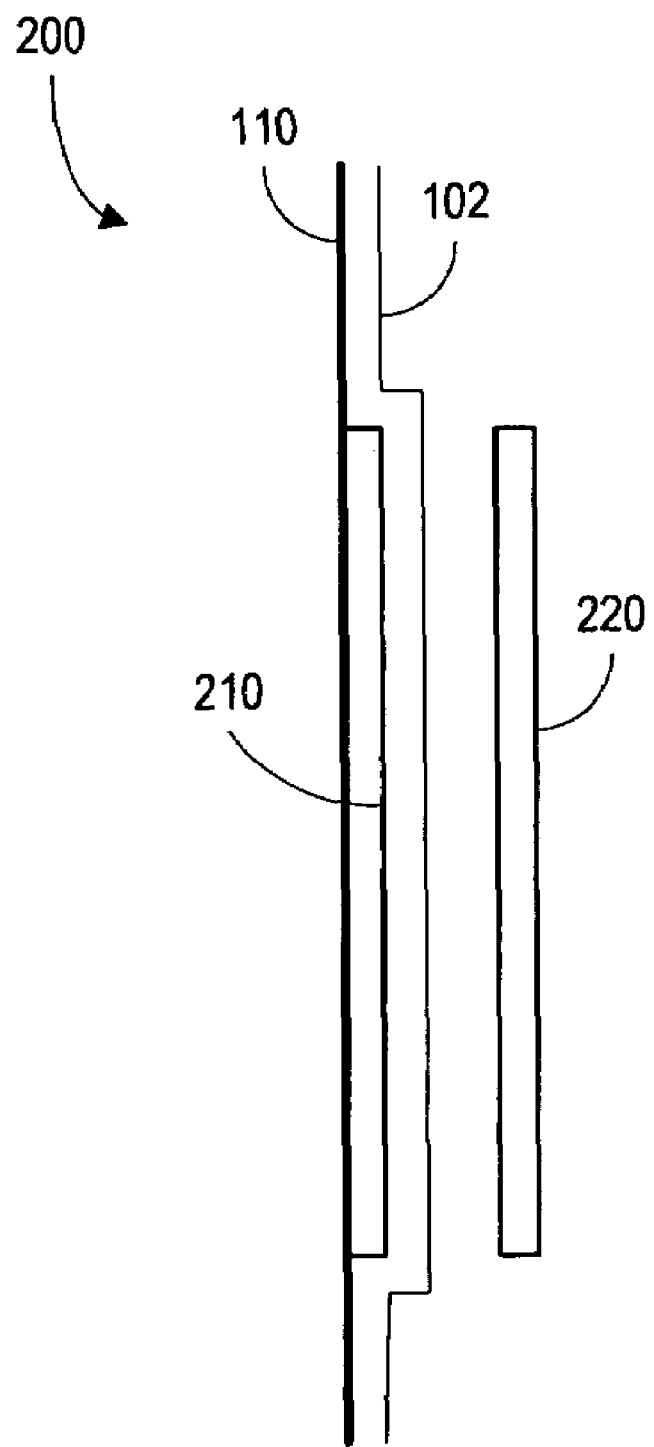
FIG. 2 is a side view of a system in accordance with an exemplary embodiment of the invention.

FIG. 2 is a side view of a system 200 in accordance with an exemplary embodiment of the invention. In particular, the system 200 includes a first capacitive element 210 associated with a surface 110 where a fouling layer 102 is to be detected. The surface 110 may, for example, be an internal surface of a heat exchanger. Note, however, that the surface 110 could instead be associated with any other types of devices that use a liquid, such as a fractionation unit or a process/water system.

The first capacitive element 210 might comprise, for example, a first conducting plate mounted onto and parallel to the surface 110. Note that a bonding or insulating layer (not illustrated in FIG. 2) might be provided between the surface 110 and the first capacitive element 210. The system 200 further includes a second capacitive element 220, such as a second conducting plate mounted substantially parallel and proximate to the first capacitive element 210.

As the fouling layer 102 grows on the surface 110, it may also grow on the first capacitive element 210. This may be especially true if the thermal characteristics of the surface 110 and the first capacitive element 210 are similar (e.g., such that they will both be at similar temperatures).

According to some embodiments, a capacitance between the first and second capacitive elements 210, 220 is used to detect formation of the fouling layer 102 (e.g., that the fouling layer 102 has reached a pre-determined thickness). Note that the fouling layer 102 may have different dielectric characteristics as compared to a fluid that is normally present between the elements 210, 220 and, therefore, the capacitance between the elements 210, 220 will change as deposits accumulate (e.g., the elements 210, 220 might act as two plates of a capacitor). By monitoring the capacitance between the elements 210, 220 the formation of the fouling layer 102 can be detected.

In this and other embodiments described herein, a scaled down device may more accurately detect formation of the fouling layer 102. For example, a very small gap between the elements 210, 220 may result in a more accurate sensor (e.g., because a small layer 102 will have a greater proportional impact on the capacitance). According to some embodiments, the elements 210, 220 may be associated with Micro-ElectroMechanical System (MEMS) devices and/or silicon micromachining technology. Such a sensor may detect a fouling layer 102 having a thickness of 1-10 micrometers or less. By sensing the fouling layer 102 at such an early stage the efficiency and maintenance costs associated with the system 200 may be improved.

Although a single pair of elements 210, 220 are illustrated in FIG. 2, note that in this and other embodiments described herein multiple systems may be used to more accurately detect formation of the fouling layer 102.

Figure 3:
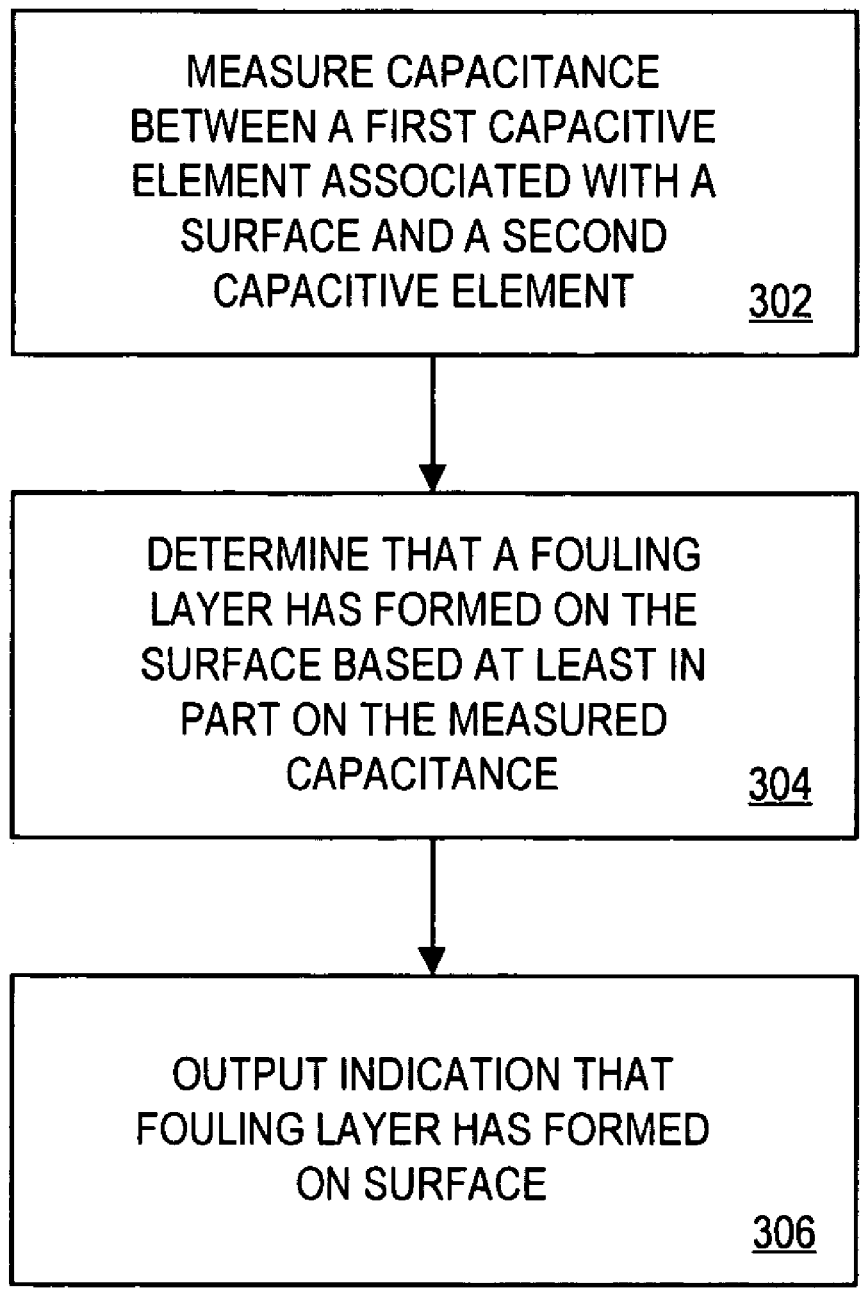
FIG. 3 is a method of detecting a fouling layer in accordance with some exemplary embodiments of the invention.

FIG. 3 is a method of detecting a fouling layer in accordance with some exemplary embodiments of the invention. At Step 302, a capacitance is measured between a first capacitive element associated with a surface and a second capacitive element. At Step 304, it is determined that a fouling layer has formed on the surface based at least in part on the measured capacitance. At Step 306, an indication that the fouling layer has formed on the surface is output. For example, a sensor might provide a binary alert signal and/or an indication of the thickness of the fouling layer.

Figure 4:
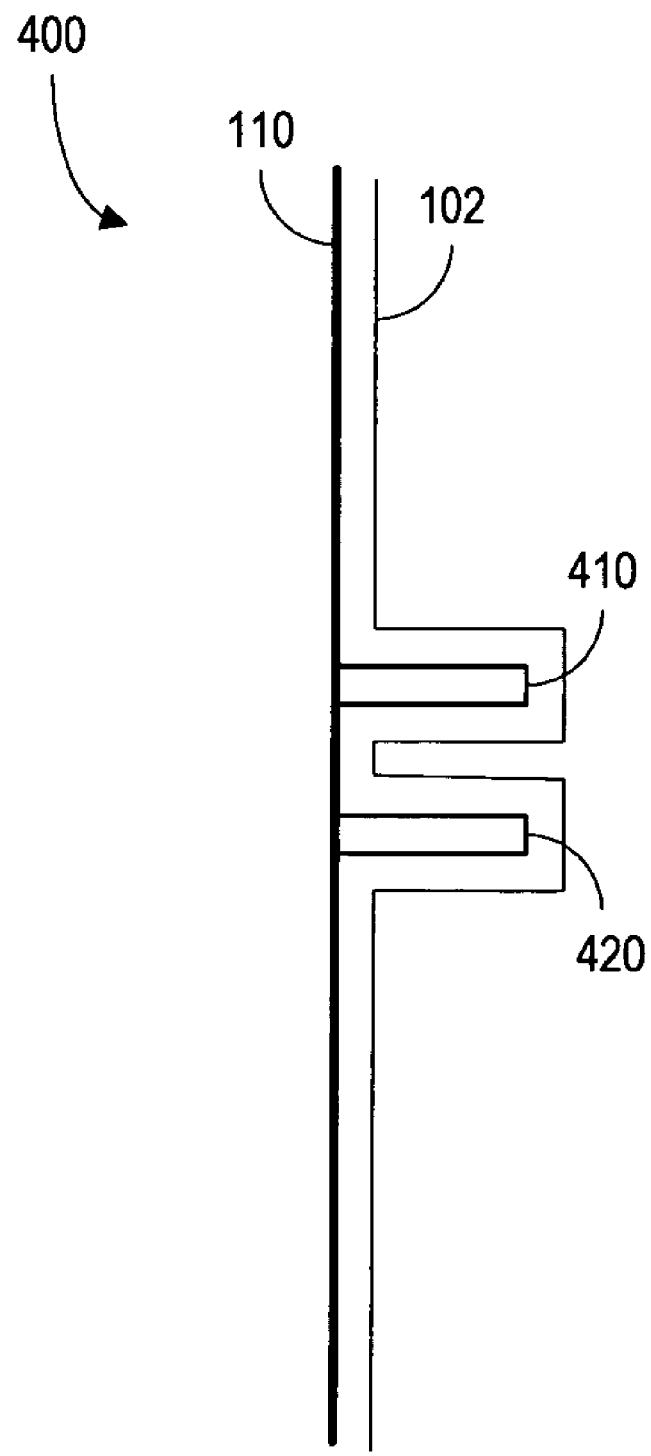
FIG. 4 is a side view of a system in accordance with an exemplary embodiment of the invention.

FIG. 4 is a side view of a system 400 in accordance with another exemplary embodiment of the invention. As before, the system 400 includes a first capacitive element 410 associated with a surface 110 where a fouling layer 102 is to be detected. The first capacitive element 410 might comprise, for example, a first conducting plate mounted onto and normal to the surface 110. Note that a bonding or insulating layer (not illustrated in FIG. 4) might be provided between the surface 110 and the first capacitive element 410. The system 400 further includes a second capacitive element 420, such as a second conducting plate mounted substantially parallel and proximate to the first capacitive element 410.

According to some embodiments, the elements 410, 420 comprise two parallel conductors by wet etching into a silicon wafer. Moreover, the elements 410, 420 may be isolated from each other, and a thin silicon oxide may be grown thermally to electrically isolate the silicon plates 410, 420 from surrounding fluid.

As the fouling layer 102 grows on the surface 110, it may also grow on the first capacitive element 410 and/or the second capacitive element 420. This may be especially true if the thermal characteristics of the surface 110 and the elements 410, 420 are similar (e.g., such that they will both be at similar temperatures). Moreover, the elements 410, 420 may need to be relatively short so that the portions of the elements 410, 420 farthest from the surface 110 will be at a temperature similar to the temperature of the surface 110 (and, therefore, will accumulate the fouling layer 102 at a similar rate).

According to some embodiments, a capacitance between the first and second capacitive elements 410, 420 is used to detect formation of the fouling layer 102. Note that the fouling layer 102 may have different dielectric characteristics as compared to a fluid that is normally present between the elements 410, 420 and, therefore, the capacitance between the elements 410, 420 will change as deposits accumulate. By monitoring the capacitance between the elements 410, 420 the formation of the fouling layer 102 can be detected.

Figure 5:
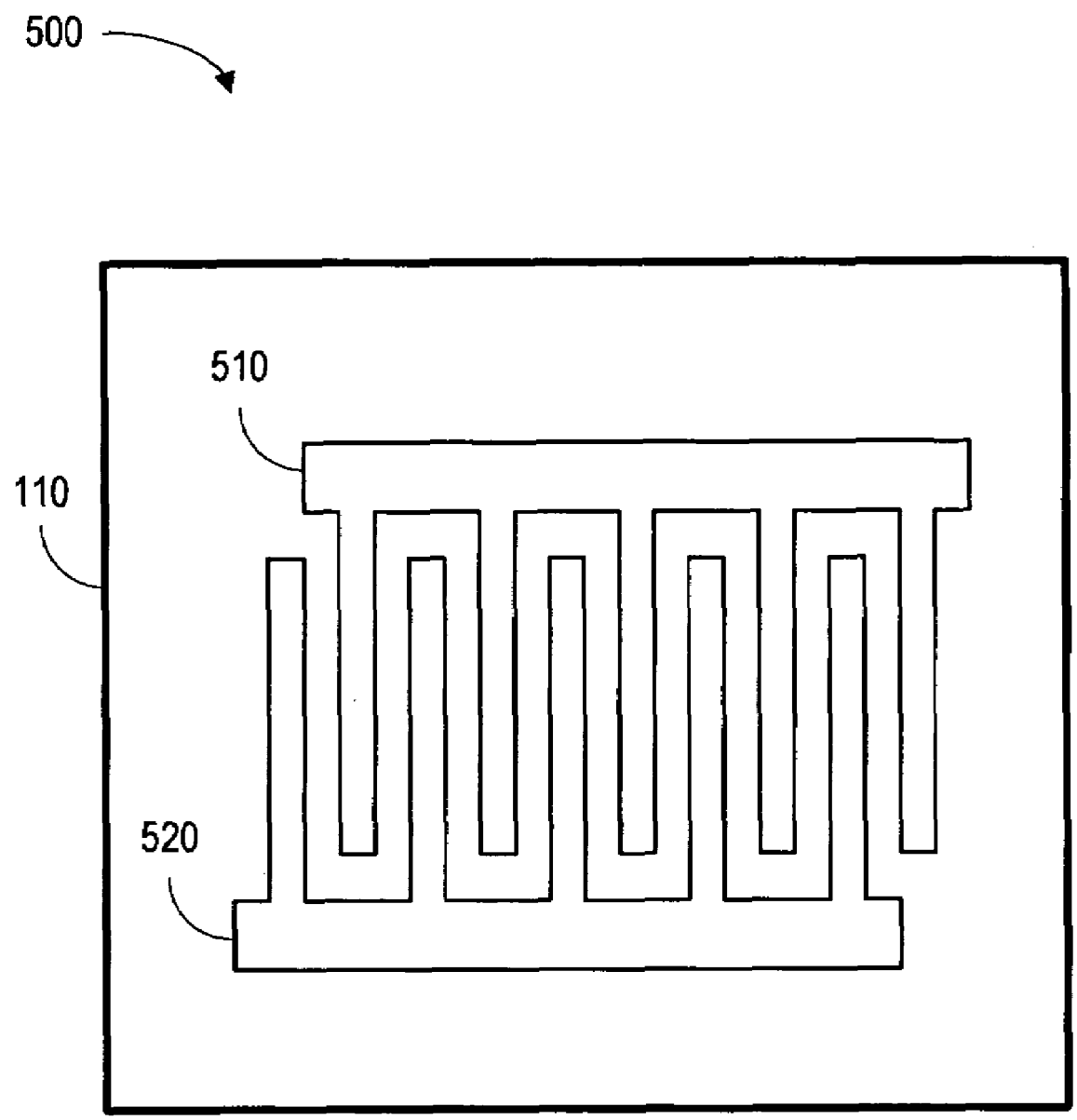
FIG. 5 is a top view of a system in accordance with another exemplary embodiment of the invention.

FIG. 5 is a top view of a system in accordance with another exemplary embodiment of the invention. As with previously described systems, the system 500 includes a first capacitive element 510 associated with a surface 110 where a fouling layer 102 is to be detected. The first capacitive element 510 might comprise, for example, a first set of conducting fingers mounted onto an parallel to the surface 110. Note that a bonding or insulating layer (not illustrated in FIG. 5) might be provided between the surface 110 and the first capacitive element 510. The system 500 further includes a second capacitive element 520, such as a second set of conducting fingers interdigitated with the fingers of the first conducting element 510. In this configuration, a fouling layer may grow on the surface 110 and the elements 510, 520 (e.g., on the surface of FIG. 5).

Note that this configuration may result in mostly fringe fields away from the plane of the elements 510, 520 (e.g., into and out of the page of FIG. 5) with a range approximately equal to the gap between the fingers. According to some embodiments, a capacitance between the first and second capacitive elements 510, 520 is used to detect formation of a fouling layer. Note that the fouling layer may have different dielectric characteristics as compared to a fluid that is normally present above the elements 510, 520 and, therefore, the capacitance between the elements 510, 520 will change as deposits accumulate on them. By monitoring the capacitance between the elements 510, 520 the formation of the fouling layer can be detected.

Figure 6:
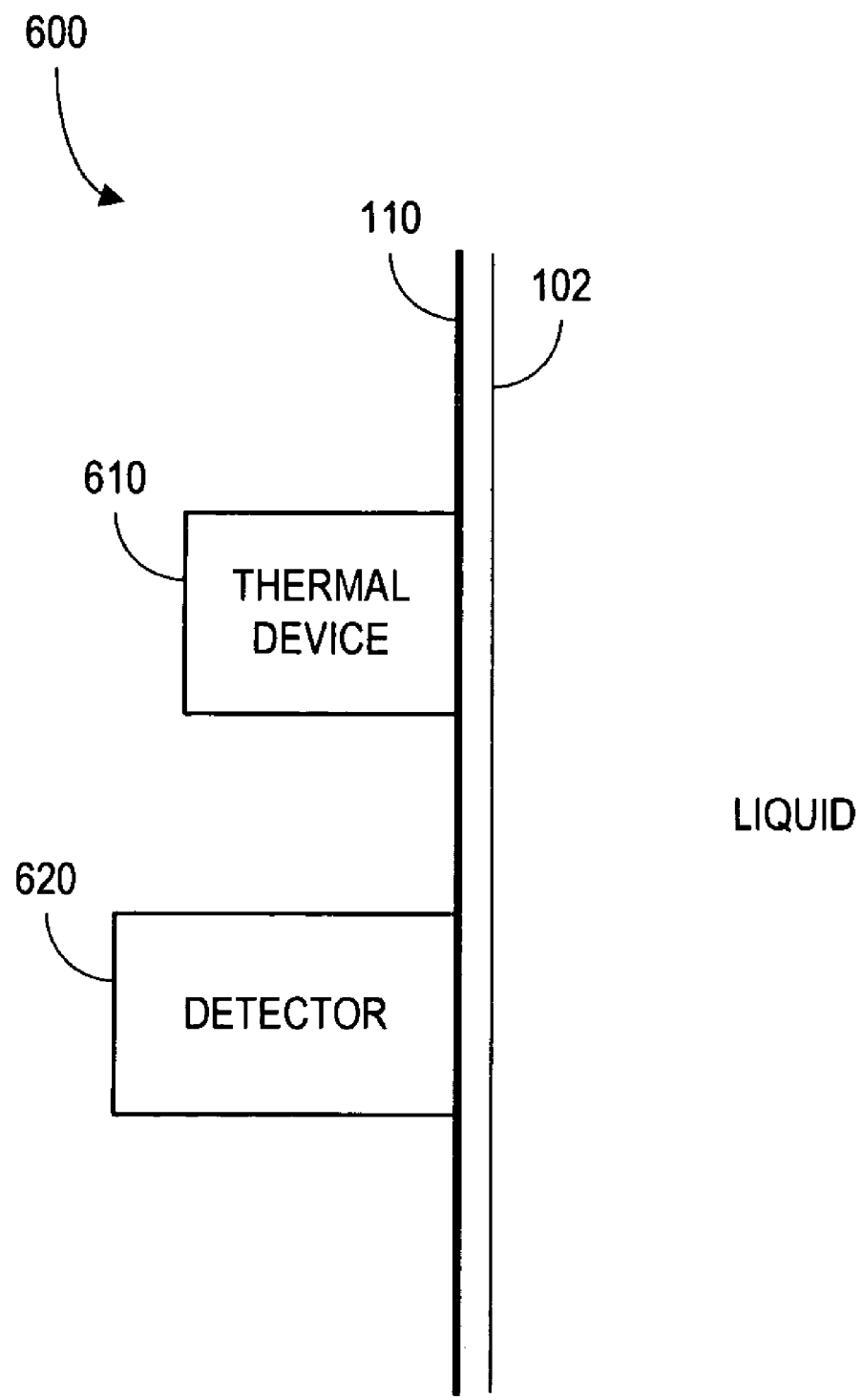
FIG. 6 is a side view of a system to detect a fouling layer in the presence of a liquid according to yet another exemplary embodiment of the invention.

FIG. 6 is a side view of a system 600 to detect a fouling layer 102 growing on a surface 110 in the presence of a liquid according to yet another exemplary embodiment of the invention. The system 600 includes a thermal device 610 to provide heat proximate to the surface 110 and a detector 620 to detect a condition associated with the surface 110. The thermal device 610 might comprise, for example, a membrane heater that is able to provide a pulse of heat to the surface 110. The detector 620 might comprise, for example, a thermometer that can determine the temperature of the surface 110. According to other embodiments, the detector 620 might measure other thermal characteristics (e.g., heat capacity and/or heat flux). As will now be described, formation of the fouling layer 102 may be determined based at least in part on the detected condition.

Figure 7:
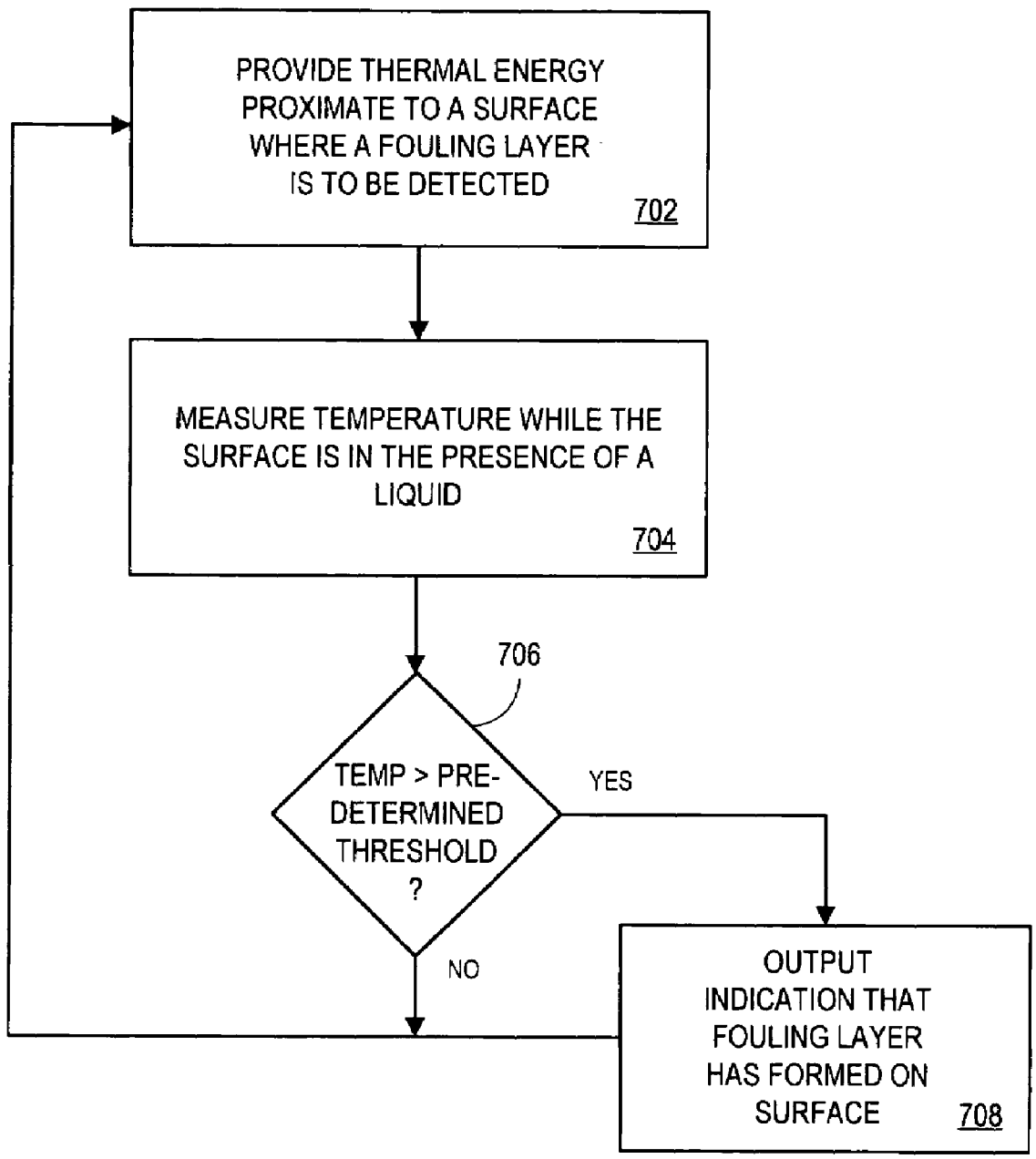
FIG. 7 is a method of detecting a fouling layer in accordance with the system of FIG. 6.

Referring to FIG. 7, which is a method of detecting the fouling layer 102 in accordance with the system 600 of FIG. 6, at Step 702 thermal energy is provided proximate to the surface 110 where the fouling layer 102 is to be detected. For example, the thermal device 610 may provide a pulse of heat while the surface 110 is in the presence of flowing water. At Step 704, a condition associated with the surface 110 is detected. For example, the detector 620 might measure the current temperature of the surface 110.

It may be determined if the fouling layer 102 has formed (e.g., is of at least a certain thickness) based at least in part on the detected condition. In particular, note that the fouling layer 102 may act as an insulator that reduces the amount of heat that may be transferred from the surface to the liquid. As a result, increasing the thickness of the fouling layer 102 will cause the surface 110 to retain more heat from the pulse generated by the thermal device 610. Thus, at Step 706 it is determined if the temperature is above a pre-determined threshold. If so, an indication that the fouling layer 102 has formed on the surface 110 is output at Step 708. The process may then be repeated (e.g., rapid pulses of heat may be applied the surface and analyzed to reduce the impact of moving liquid in the system 600).

Figure 8:
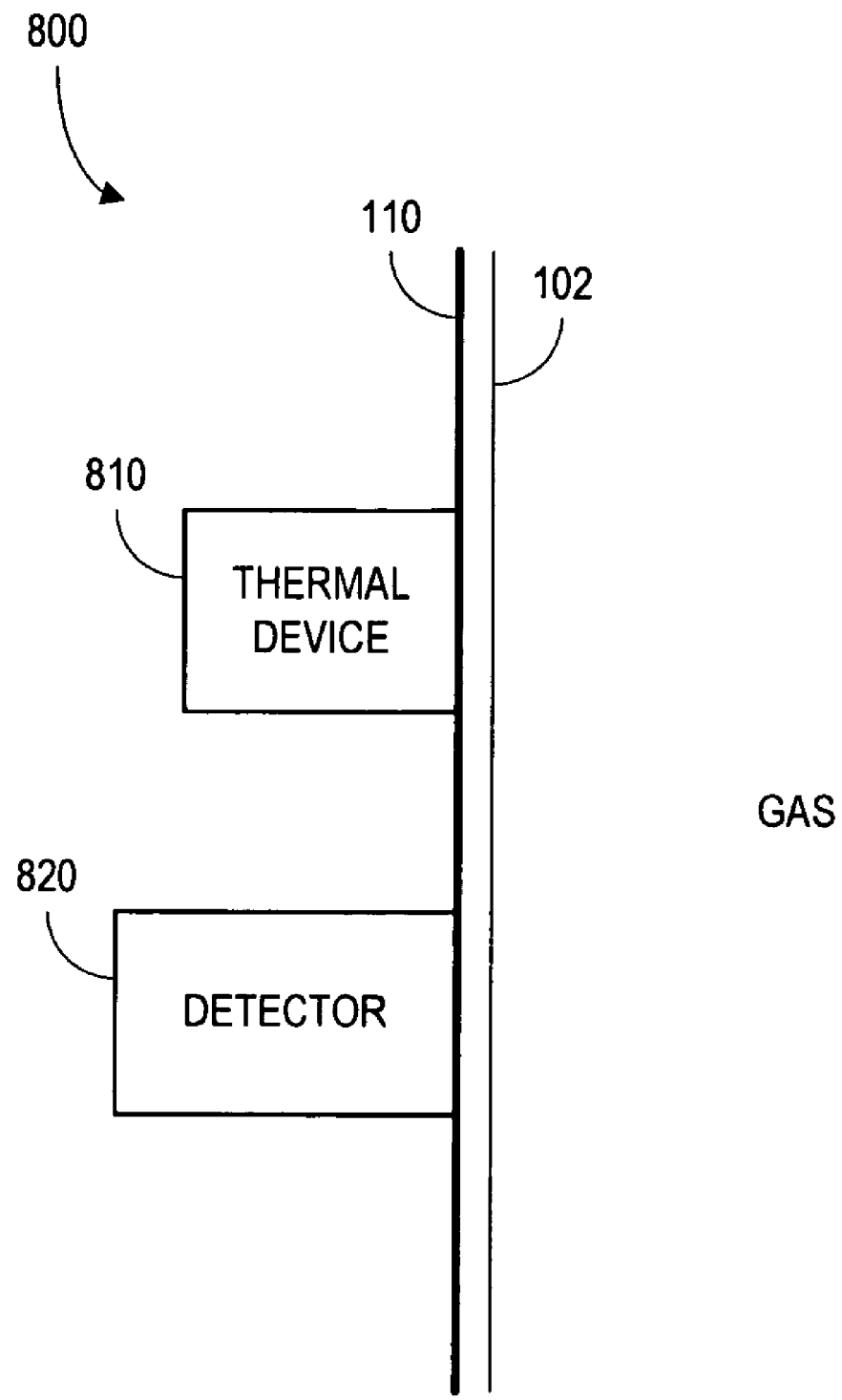
FIG. 8 is a side view of a system to detect a fouling layer in the presence of a gas according to yet another exemplary embodiment of the invention.

Note that the presence of moving liquid in the system 600 may make it difficult to accurately determine small temperature changes. FIG. 8 is a side view of a system 800 to detect a fouling layer 102 growing on a surface 110 in the presence of a gas according to yet another exemplary embodiment of the invention. The system 800 includes a thermal device 810 to provide heat proximate to the surface 110 and a detector 820 to detect a condition associated with the surface 110. The thermal device 810 might comprise, for example, a membrane heater that is able to provide a pulse of heat to the surface 110. The detector 820 might comprise, for example, a thermometer that can determine the temperature of the surface 110. According to other embodiments, the detector 820 might measure other thermal characteristics (e.g., heat capacity and/or heat flux). As will now be described, formation of the fouling layer 102 may be determined based at least in part on the detected condition.

Figure 9:
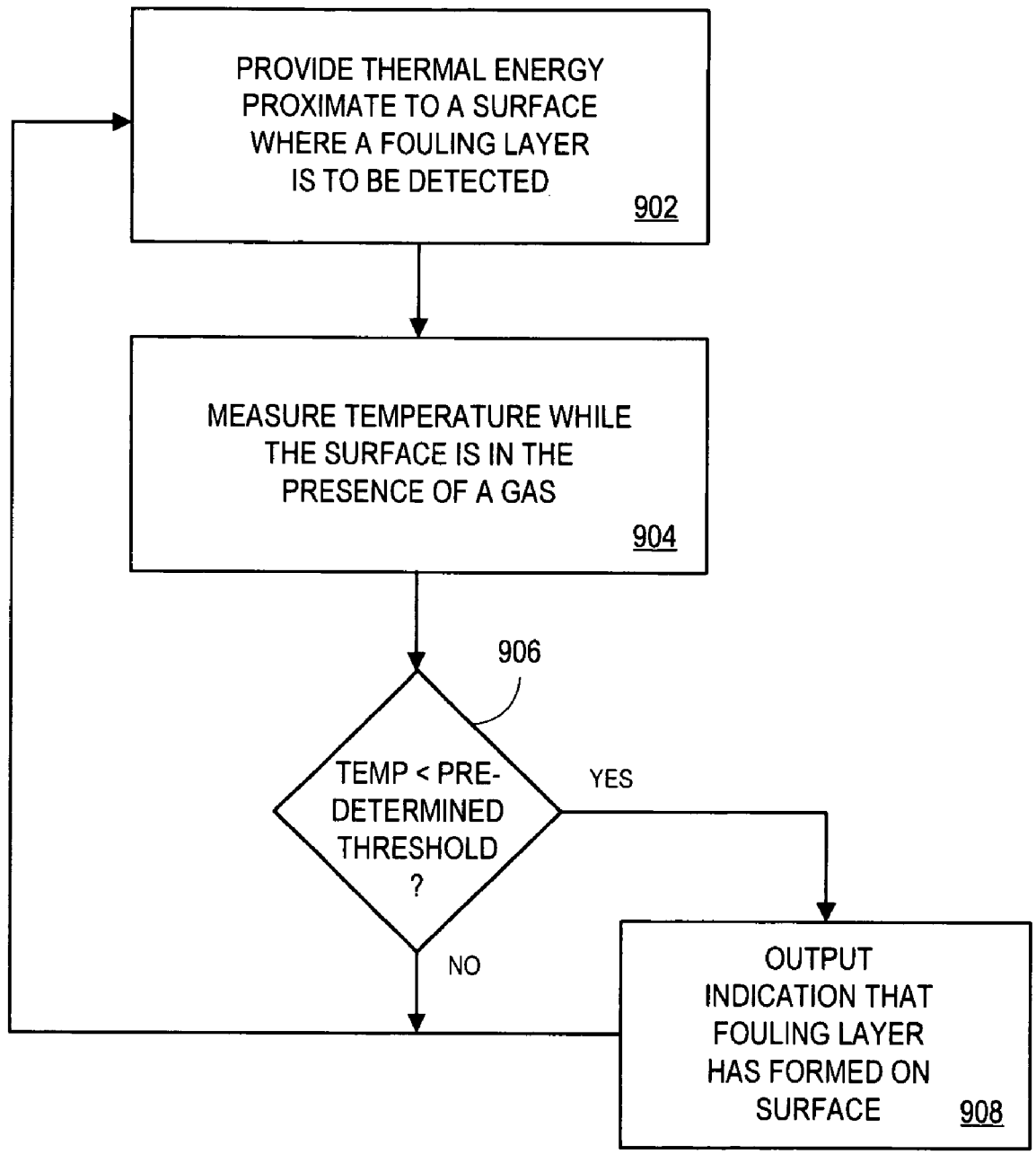
FIG. 9 is a method of detecting a fouling layer in accordance with the system of FIG. 8.

Refer to FIG. 9, which is a method of detecting the fouling layer 102 in accordance with the system 800 of FIG. 8. At Step 902, thermal energy is provided proximate to the surface 110 where the fouling layer 102 is to be detected. For example, the thermal device 810 may provide a pulse of heat after water has been removed from a chamber (and now the chamber contains only air). At Step 904, a condition associated with the surface 110 is detected. For example, the detector 820 might measure the current temperature of the surface 110.

It may be determined if the fouling layer 102 has formed (e.g., is of at least a certain thickness) based at least on part on the detected condition. In particular, note that the fouling layer 102 may act as thermal load that absorbs some of the heat received from the thermal device 810. As a result, increasing the thickness of the fouling layer 102 will cause the surface 110 to retain less heat from the pulse generated by the thermal device 810. Thus, at Step 906 it is determined if the temperature is below a pre-determined threshold. If so, an indication that the fouling layer 102 has formed on the surface 110 is output at Step 908.

Figure 10:
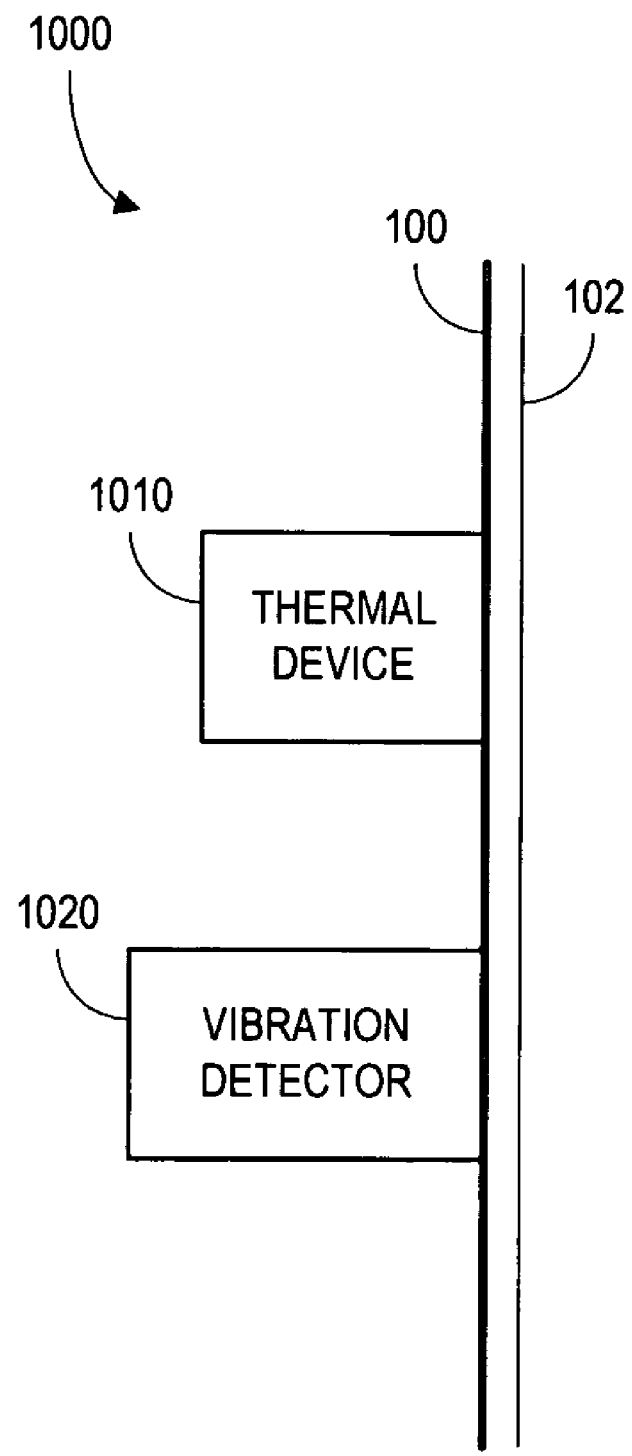
FIG. 10 is a side view of a system to detect a fouling layer using vibration according to yet another exemplary embodiment of the invention.

Note that conditions other than temperature changes might be monitored to detect a fouling layer. FIG. 10 is a side view of a system 1000 to detect a fouling layer 102 growing on a surface 110 according to yet another exemplary embodiment of the invention. The system 1000 includes a thermal device 1010 to provide heat proximate to the surface 110 and a vibration detector 1020 to detect a condition associated with the surface 110. The thermal device 1010 might comprise, for example, a membrane heater that is able to provide heat pulses to the surface 110. The vibration detector 1020 might comprise, for example, a device that can determine vibration-related characteristics of the surface 110. As will now be described, formation of the fouling layer 102 may be determined based at least in part on the detected condition.

Figure 11:
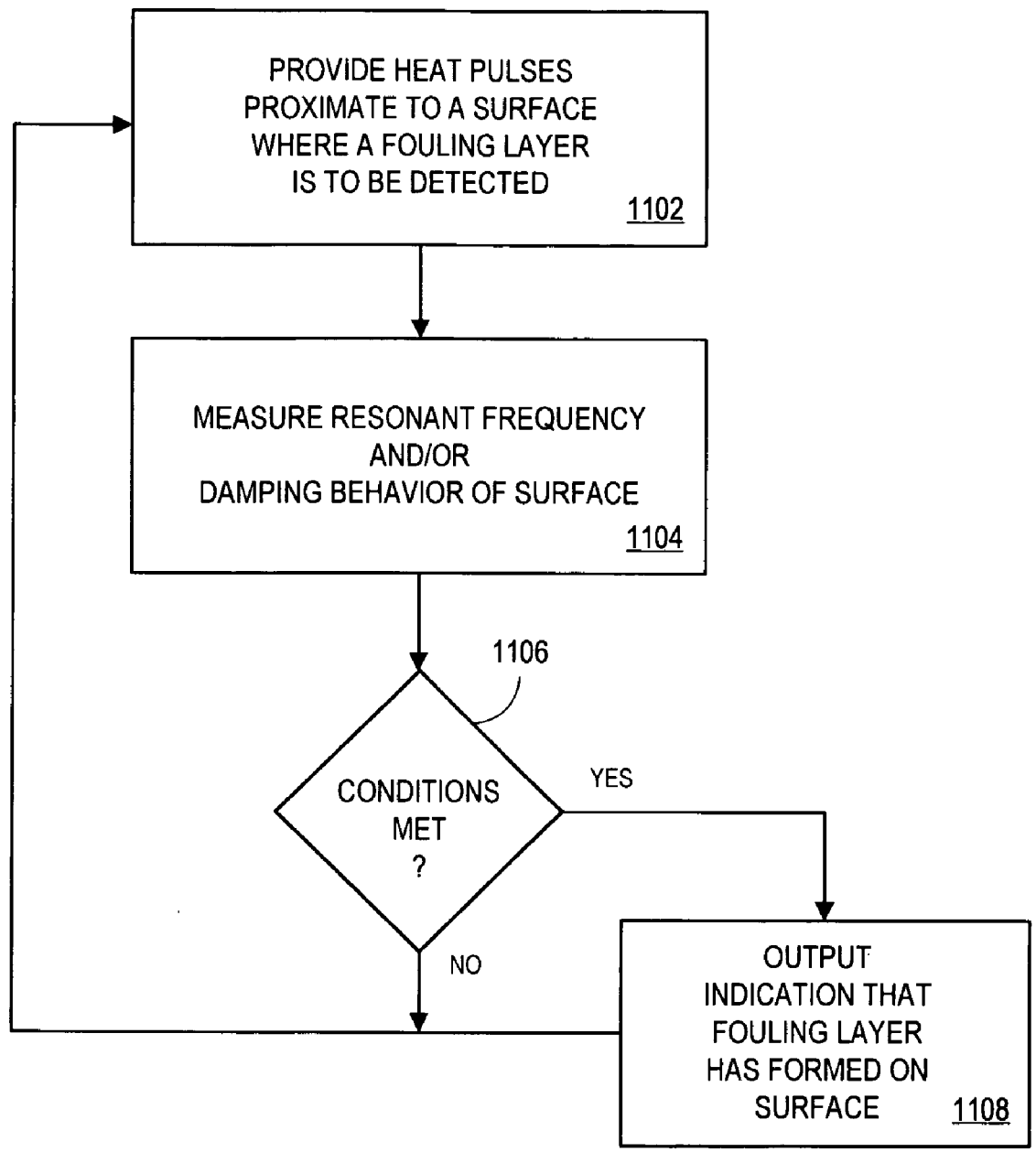
FIG. 11 is a method of detecting a fouling layer in accordance with the system of FIG. 11.

Refer to FIG. 11, which is a method of detecting the fouling layer 102 in accordance with the system 1000 of FIG. 10. At Step 1102, thermal energy is provided proximate to the surface 110 where the fouling layer 102 is to be detected. For example, the thermal device 1010 may provide pulses of heat while the surface 110 is in the presence of either a liquid or a gas. Assuming the surface 110 and fouling layer 102 have different thermal coefficients of expansion, these pulses may cause the surface 110 to vibrate. According to other embodiments, an oscillator (not illustrated in FIG. 10) may be used to induce vibration of the surface 110 instead of the thermal device 1010.

At Step 1104, a condition associated with the surface 110 is detected. For example, the vibration detector 1020 might measure information associated with a resonant frequency and/or a damping behavior of the surface 110.

It may be determined if the fouling layer 102 has formed (e.g., is of at least a certain thickness) based at least on part on the detected condition. In particular, note that the fouling layer 102 may act alter the resonant frequency and/or damping behavior of the surface 110. Thus, at Step 1106 it is determined if certain vibration-related conditions are met. If so, an indication that the fouling layer 102 has formed on the surface 110 is output at Step 1108.

By detecting a fouling layer at an early stage of build up in accordance with any of the embodiments described herein, a maintenance frequency associated with a heat exchange or other types of devices may be reduce. Moreover, the need for factory shut downs may be avoided and/or the energy efficiency of such devices may be improved.

The following illustrates various additional embodiments of the invention. These do not constitute a definition of all possible embodiments, and those skilled in the art will understand that the present invention is applicable to many other embodiments. Further, although the following embodiments are briefly described for clarity, those skilled in the art will understand how to make any changes, if necessary, to the above-described apparatus and methods to accommodate these and other embodiments and applications.

Several approaches to early fouling detection have been provided, and any of the embodiments described here may be used together with other approaches. For example, a sensor may use both capacitance detection (e.g., as described with respect to FIG. 2) and thermal detection (e.g., as described with respect to FIG. 6). Moreover, although particular layouts and configurations have been provided, embodiments described herein may be implements using any number of other layouts and configurations.

The present invention has been described in terms of several embodiments solely for the purpose of illustration. Persons skilled in the art will recognize from this description that the invention is not limited to the embodiments described, but may be practiced with modifications and alterations limited only by the spirit and scope of the appended claims.

What is claimed:

1. An apparatus, comprising:
    a first capacitive element associated with a surface where a non-fluid fouling layer is to be detected, the first capacitive element comprising a first conducting plate mounted onto and parallel to the surface; and
    a second capacitive element comprising a second conducting plate mounted substantially parallel and proximate to the first conducting plate, wherein the first conducting plate exhibits similar thermal response as compared to the surface where the fouling layer is to be detected and wherein a capacitance between the first and second capacitive elements is to be used to detect formation of the fouling layer.

2. The apparatus of claim 1, wherein the first capacitive element comprises a first conducting plate mounted onto and substantially normal to the surface and the second capacitive element comprises a second conducting plate mounted onto the surface, wherein the second conducting plate is substantially parallel and proximate to the first conducting plate.

3. The apparatus of claim 2, wherein the first and second conducting plates exhibit similar thermal responses as compared to the surface where the fouling layer is to be detected.

4. The apparatus of claim 1, wherein the first capacitive element comprises a first set of conducting fingers, the second capacitive element comprises a second set of conducting fingers, wherein the first and second sets of fingers are interdigitated and mounted onto and parallel to the surface.

5. The apparatus of claim 4, wherein the capacitance between the first and second sets of fingers is associated with a capacitance transduction.

6. The apparatus of claim 4, wherein at least one of the first and second sets of fingers exhibit a similar thermal response as compared to the surface where the fouling layer is to be detected.

7. The apparatus of claim 1, wherein the apparatus comprises a micro-electromechanical sensor.

8. The apparatus of claim 7, wherein the surface is associated with at least one of: (i) a heat exchanger, (ii) a fractionation unit, or (iii) a process/water system.

9. An apparatus, comprising:
    a surface where a fouling layer is to be detected;
    a heater; and
    a detector to detect a condition associated with the surface, wherein formation of the fouling layer is determined based at least in part on the condition; wherein the heater provides a heat pulse while the surface is in the presence of a liquid and it is determined that the fouling layer has formed when the detector detects a temperature above a pre-determined threshold.

10. The apparatus of claim 9, wherein the detector is a vibration detector.

11. The apparatus of claim 10, wherein it is determined that the fouling layer has formed based at least in part on at least one of: (i) a resonate frequency, or (ii) damping behavior.

* * * * *

UNITED STATES PATENT AND TRADEMARK OFFICE
CERTIFICATE OF CORRECTION

PATENT NO. : 7,652,586 B2
APPLICATION NO. : 11/504739
DATED : January 26, 2010
INVENTOR(S) : Baller et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 686 days.

Signed and Sealed this

Twenty-eighth Day of December, 2010

David J. Kappos
*Director of the United States Patent and Trademark Office*